United States Patent [19]

Bosshard et al.

[11] 4,154,743

[45] May 15, 1979

[54] 3-OXOBENZOFURANYL-2-IDENYL, HALOACETIC ACIDS

[75] Inventors: Hans Bosshard, Basel; Niklaus Bühler, Rheinfelden, both of Switzerland

[73] Assignee: Ciba-Geigy Corporation, Ardsley, N.Y.

[21] Appl. No.: 876,377

[22] Filed: Feb. 9, 1978

[30] Foreign Application Priority Data

Feb. 11, 1977 [LU] Luxembourg .......................... 76756

[51] Int. Cl.² ............................................ C07D 307/83
[52] U.S. Cl. ........................ 260/346.71; 260/306.7 R; 260/307 FA; 260/326.34; 260/346.22; 260/346.73; 544/54; 544/58; 544/96; 544/153; 544/333; 544/376; 548/300; 546/196
[58] Field of Search ..................... 260/346.22, 346.71, 260/346.73, 330.5, 293.58, 306.7 R, 307 FA, 326.34; 544/54, 58, 96, 153, 333, 376; 548/300

[56] References Cited

U.S. PATENT DOCUMENTS 3,629,290  12/1971  Cairns et al. ..................... 260/345.2
3,816,467  6/1974   Wright ............................ 260/346.71

OTHER PUBLICATIONS

Chem. Abst. 53, 5186d, (1959).
E. Ziegler et al., Liebigs Ann. Chem. 1973, pp. 1552-1556.

Primary Examiner—Natalie Trousof
Assistant Examiner—Bernard Dentz
Attorney, Agent, or Firm—Luther A. R. Hall

[57] ABSTRACT

Novel halogeno-benzofuranone-carboxylic acids and a novel process for their preparation by reacting substituted or unsubstituted phenols with dihalogenomaleic anhydrides or derivatives thereof are described. The novel halogeno-benzofuranone-carboxylic acids are valuable intermediates for the preparation of pharmaceutical active compounds having an antiallergic action or for the preparation of biocidal active compounds for combating plant and animal pests, in particular phytopathogenic fungi and bacteria.

10 Claims, No Drawings

3-OXOBENZOFURANYL-2-IDENYL, HALOACETIC ACIDS

The present invention relates to novel halogeno-benzofuranone-carboxylic acids and to a novel process for their preparation.

The novel halogeno-benzofuranone-carboxylic acids are of the formula I

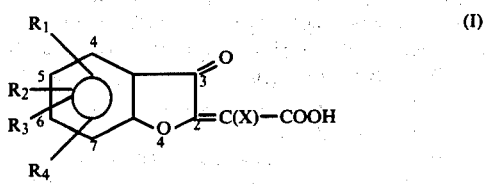

in which X is chlorine, bromine or fluorine, $R_1$ and $R_2$ independently of one another are hydrogen or a lower alkyl group, $R_3$ is hydrogen, a halogen atom or a hydroxyl or lower alkyl group and $R_4$ is hydrogen, a halogen atom or a hydroxyl, carboxyl, lower alkyl, lower alkoxy, phenoxy, cycloalkyl or acyl group or a substituted or unsubstituted amino group, or, if $R_3$ and $R_4$ are hydrogen, $R_1$ and $R_2$ together with the bonding C atoms in the ortho-position form a cycloalkyl group or a fused benzene ring.

The compounds according to the invention, of the formula I, can be in the form of the cis or the trans isomers or in the form of mixtures of cis/trans isomers relative to the exocyclic C=C double bond. Mixtures of isomers of this type can be separated into their constituents on the basis of the differences in the physico-chemical properties, in a conventional manner, for example by chromatography or by fractional crystallisation.

The compounds of the formula I can be prepared in high purity in a simple and economic manner using readily accessible starting materials and in good to very good yields by reacting a compound of the formula II

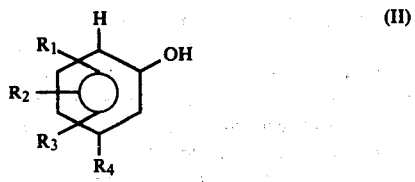

in the presence of a Lewis acid with a compound of the formula III

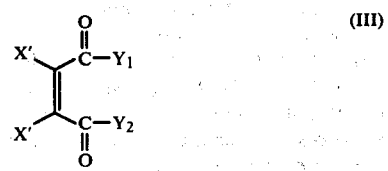

to give a compound of the formula IV

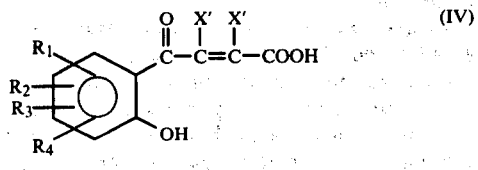

and subsequently cyclising the compound of the formula IV to a compound of the formula I.

In the above formulae II–IV, $R_1$, $R_2$, $R_3$ and $R_4$ are as defined under formula I, in formulae III and IV, the two X′ independently of one another are chlorine, bromine or fluorine and one of $Y_1$ and $Y_2$ is halogen, especially chlorine or bromine, and the other is —OH or —O—alkyl having 1–6 C atoms, or $Y_1$ and $Y_2$ together form the grouping —O—.

According to the process of the invention it is, surprisingly, not the 6-membered ring, which is to be expected according to the literature data, which is formed during the cyclisation, with the formation of a chromanone or chromone derivative, but the 5-membered ring according to the definition, which has an exocyclic double bond. That is to say, it is known from the literature that 3-(hydroxybenzoyl)-acrylic acid can be prepared in 2.5 to 4% yield by a Friedel-Crafts acylation of phenol with maleic anhydride at 20° C. Under the action of alkali, such as $Na_2CO_3$, this acid can be converted into the 4-chromanone-2-carboxylic acid, which, in turn, can be dehydrogenated to chromone-2-carboxylic acid [c.f. for example, CA, 53,5186d(1959) and Liebigs Annalen Chem., 177, 1552-53(1973) and also German Offenlegungsschrift No. 1,802,961].

In formula I X is preferably bromine and especially chlorine. $Y_1$ and $Y_2$ together preferably form the grouping —O—.

Lower alkyl or lower alkoxy groups as $R_1$ to $R_4$ have in particular 1–7 and preferably 1–4 carbon atoms, such as the methyl, ethyl, n-propyl, isopropyl, n-butyl, n-pentyl, n-heptyl, methoxy, ethoxy, n-propoxy, isopropoxy, n-butoxy, tert.-butoxy, n-pentyloxy and n-hexyloxy group. Particularly preferred lower alkyl and lower alkoxy groups have 1 or 2 carbon atoms, in particular the methyl group and the methoxy group.

If $R_3$ and $R_4$ is a halogen atom, this is, for example, a fluorine atom, but especially a bromine or chlorine atom.

Fused benzene rings formed by $R_1$ and $R_2$ together with bonding C atoms can be unsubstituted or substituted, for example by halogen atoms, in particular chlorine, or alkyl groups, especially those having 1 or 2 carbon atoms.

Preferably, however, $R_1$ and $R_2$ in formula I, together with the bonding C atoms, form an unsubstituted benzene ring bonded in the 4,5-position.

If, when $R_3$ and $R_4$=H, $R_1$ and $R_2$, together with the bonding C atoms in the ortho-position, form a cycloalkyl group, this has in particular 5–7 ring members and can be substituted, for example by alkyl groups having 1–4 and especially 1 or 2 carbon atoms. Preferably, however, cycloalkyl groups of this type are unsubstituted and bonded in the 5,6-position of the benzofuranone; in particular, $R_1$ and $R_2$ together with the bonding C atoms form a cyclopentane or cyclohexane ring bonded in the 5,6-position.

Preferred cycloalkyl groups $R_4$ are unsubstituted cycloalkyl groups having 5 to 8 ring carbon atoms, such as the cyclopentyl, cycloheptyl and cyclooctyl group and in particular the cyclohexyl group.

Phenoxy groups $R_4$ are preferably unsubstituted but can also be substituted by alkyl or alkoxy groups having 1–4 and especially 1 or 2 carbon atoms, such as the methyl or methoxy group, or by halogen atoms, for example chlorine.

Acyl groups $R_4$ are derived, for example, from aliphatic, carbocyclic-aromatic or heterocyclic-aromatic carboxylic acids. In particular they are aroyl and alkanoyl groups, for example benzoyl groups, which can be substituted by alkyl or alkoxy groups having 1-4 and especially 1 or 2 carbon atoms or by halogen atoms, such as chlorine, but are preferably unsubstituted, or —CO-alkyl groups having 1-6 and especially 1-3 carbon atoms in the alkyl part, such as the acetyl, propionyl, butyryl, valeroyl and pivaloyl group.

If $R_4$ is a substituted amino group, possible groups are, in particular, groups of the formulae

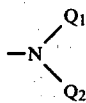

and —NHCO—$Q_3$ in which $Q_3$ is lower alkyl, $Q_1$ is hydrogen or lower alkyl and $Q_2$ is lower alkyl, or $Q_1$ and $Q_2$ together are alkylene having 4-7 carbon atoms, which can be interrupted —S—, —O— or

in which $Q_4$ is hydrogen or lower alkyl. Lower alkyl groups as $Q_1$ to $Q_4$ have in particular 1-6 and preferably 1-4 carbon atoms. Particularly preferentially $Q_1$, $Q_2$ or $Q_3$ are methyl or ethyl, or $Q_1$ and $Q_2$ together are the grouping —(CH$_2$)$_4$—, —(CH$_2$)$_5$—, —(CH$_2$)$_2$O(CH$_2$)$_2$— or

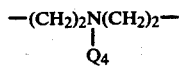

and $Q_4$ is hydrogen or methyl.

If one of $R_1$ to $R_4$ is hydrogen, the remaining substituents in the compounds of the formula I are preferably in the 5-, 6- and/or 7-position. According to a further preference, two of the substituents $R_1$ to $R_4$ are hydrogen and the remaining substituents are in the said preferred positions, especially in the 5- and/or 6-position.

Preferred compounds of the formula I are those in which X is chlorine, $R_1$ and $R_2$ independently of one another are hydrogen or an alkyl group having 1-4 and especially 1 or 2 carbon atoms, $R_3$ is hydrogen, chlorine, fluorine, bromine or an alkyl group having 1-4 and especially 1 or 2 carbon atoms and $R_4$ is hydrogen, chlorine, fluorine, bromine, —OH, —COOH, cyclohexyl, an alkyl or alkoxy group having 1-4 and in particular 1 or 2 carbon atoms, an alkanoyl group having 2-7 carbon atoms, for example acetyl, an alkanoylamino group having 2-4 carbon atoms, for example acetylamino, or a N,N-dialkylamino group having 1 or 2 carbon atoms in each alkyl part.

Preferred compounds of the formula I are also those in which X is chlorine, $R_3$ and $R_4$ are hydrogen and $R_1$ and $R_2$ together form an alkylene group having 3-5 carbon atoms which is bonded in the 5,6-position or a 1,4-butadienyl group bonded in the 4,5-position.

According to a further preference, $R_1$, $R_2$ and $R_3$ independently of one another are hydrogen and $R_4$ is hydrogen, alkyl or alkoxy having 1-4 and especially 1 or 2 carbon atoms, —OH, chlorine, fluorine, bromine or cyclohexyl.

Particularly preferred compounds are those of the formula Ia

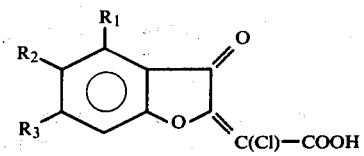

in which $R_1$ and $R_2$ independently of one another are hydrogen or alkyl having 1-4 carbon atoms, such as methyl, and $R_3$ is hydrogen, alkyl or alkoxy having 1-4 carbon atoms, such as methyl and methoxy, or —OH, or in which $R_1$ and $R_2$ together form 1,4-butadienylene and $R_3$ is hydrogen, or $R_1$ is hydrogen and $R_2$ and $R_3$ together form alkylene having 3 or 4 carbon atoms, for example 1,3-propylene.

Very particularly preferred compounds are those of the formula Ia in which $R_1$ is hydrogen or methyl and one of the radicals $R_2$ and $R_3$ is methyl and the other is hydrogen or methyl, or in which $R_1$ is hydrogen and $R_2$ and $R_3$ together are trimethylene.

The starting materials of the formula II and III are known per se or can be prepared by conventional methods. Compounds of the formula III which are preferably used are those in which the two X' have the same meaning and $Y_1$ and $Y_2$ together are the grouping —O—, and in particular dichloromaleic anhydride.

Examples of Lewis acids which can be used when reacting the compounds of the formula II with the compound of the formula III are: aluminium chloride, aluminium bromide, zinc chloride, tin tetrachloride, boron trifluoride, iron-III chloride, titanium tetrachloride, phosphorus trichloride, phosphorus oxychloride, antimony pentafluoride and antimony pentachloride. Aluminium chloride is preferably used.

The Lewis acid is appropriately employed in excess, for example in about 2 times to 10 times the molar amount. The reactants of the formula II and III are preferably employed in substantially stoichiometric amounts.

The reaction to give the intermediates of the formula IV can be carried out in an inert organic solvent or in the melt. Suitable organic solvents are, for example: chlorinated aliphatic or aromatic hydrocarbons, such as methylene chloride, 1,2-dichloroethane, 1,2,3-trichloropropane, 1,1,2,2-tetrachloroethane and o-dichlorobenzene; n-pentane and n-hexane; nitromethane, nitrobenzene and carbon disulphide.

The reaction in the melt is appropriately carried out in the presence of low-melting salt mixtures, for example mixtures of aluminium chloride with inorganic or organic salts, such as ammonium halides, alkaline earth metal halides and alkali metal halides, for example ammonium chloride, magnesium chloride and calcium chloride, but especially sodium chloride and potassium chloride, and also pyridinium salts, for example N-alkylpyridinium halides. Eutectic salt mixtures, especially mixtures of aluminium chloride and sodium chloride and/or potassium chloride, are preferred. However, in themselves any desired salt mixtures can be employed if an adequate lowering of the melting point is achieved therewith.

In general, the reaction temperatures are between about 0° and 130° C. For the reaction in an inert organic solvent, reaction temperatures of between about 0° and 90° C. are preferred, depending on the nature of the solvent. In most cases, however, the reaction in the presence of an inert organic solvent can already be carried out at temperatures of between about 0° and 30° C.

The reaction in the melt is advantageously carried out at temperatures of between about 70° and 120° C.

Preferably, the reaction is carried out in an inert organic solvent, especially methylene chloride, 1,2-dichloroethane or 1,1,2,2-tetrachloroethane, or alternatively in the melt with the addition of sodium chloride and/or potassium chloride.

After the reaction has ended, the resulting complex is appropriately decomposed by pouring it into a water-/ice mixture or by adding a dilute mineral acid, such as hydrochloric acid, with cooling, and the solvent, if present, is removed.

In most cases, the intermediates of the formula IV can be isolated, and purified, in a manner which is conventional per se. However, isolation and purification of this type is not necessary.

The cyclisation of the compounds of the formula IV with elimination of HX' can be carried out in an organic or aqueous-organic medium. However, the cyclisation is preferably carried out in an aqueous medium. The cyclisation temperature and time can vary greatly depending on the nature of the intermediate of the formula IV and of the reaction medium chosen.

Mixtures of a base, such as pyridine or triethylamine, with suitable inert organic solvents and, if desired, water are appropriately used for the cyclisation in an organic or aqueous-organic medium. Suitable inert organic solvents are, for example, aliphatic or aromatic hydrocarbons which can be chlorinated, and alkanols, such as methanol, ethanol, 1,2-dichloroethane, benzene, toluene and chlorobenzene; aliphatic or cyclic ethers, such as diethyl ether, tetrahydrofurane and dioxane; ethylene glycol monoalkyl and dialkyl ethers having, in each case, 1–4 carbon atoms in the alkyl parts, such as ethylene glycol monomethyl ether and ethylene glycol monoethyl ether, ethylene glycol dimethyl ether and ethylene glycol diethyl ether.

In some cases the cyclisation can be carried out in a strongly acid to neutral aqueous medium (pH between about 0 and 7) and at a temperature of up to about 100° C.

If, when $R_3$ and $R_4$=H, $R_1$ and $R_2$, together with the bonding C atoms, form, for example, a fused benzene ring, the corresponding intermediate of the formula IV can even be cyclised by simply pouring it into dilute aqueous mineral acids.

Preferably, however, the cyclisation is carried out in an aqueous medium in the presence of an organic or inorganic base. Examples of bases which can be used are tertiary amines, such as trimethylamine or triethylamine, pyridine, pyridine bases or alkali metal hydroxides or carbonates and alkaline earth metal hydroxides or carbonates; alkali metal hydroxides are preferred, especially sodium hydroxide and potassium hydroxide. The reaction temperatures are appropriately between about 0° and 60° C. and preferably between about 0° and 30° C.

According to a particularly preferred embodiment, the cyclisation is carried out in an aqueous medium with the addition of, advantageously, 4 to 6 mols of an alkali metal hydroxide, especially sodium hydroxide or potassium hydroxide, per mol of intermediate of the formula IV at a temperature of between about 0° and 30° C. At a reaction temperature of about 25°–30° C. the reaction has generally ended within a few minutes; at about 0° C. the reaction takes about one to two hours. Particularly high yields and pure products are achieved with this embodiment. It is surprising that, in the cyclisation according to the invention, it is not the expected 6-membered ring but a 5-membered ring having an exocyclic C=C double bond which is formed and that, in an alkaline medium, although the second halogen atom has a high reactivity towards nucleophilic agents, for example towards hydroxyl ions in an aqueous-alkaline medium, this atom is not also detached.

After the reaction has ended, the compounds of the formula I can be isolated in a conventional manner, for example by acidifying the reaction mixture with hydrochloric acid, filtering and washing with water. The compounds of the formula I obtained by the process according to the invention in general contain only slight impurities and can be used direct for preparative purposes.

If desired, they can be converted to the analytically pure form by recrystallisation from suitable solvents, such as acetic acid, ethyl acetate, methanol, ethanol, dioxane or toluene. The compounds of the formula I are obtained in the form of pale yellow to orange coloured crystals and are valuable intermediates for the preparation of pharmaceutical active compounds having an antiallergic action, for example 3-hydroxy-benzofuryl-2-glyoxylic acids and esters or salts thereof.

The preparation of several pharmaceutical active compounds which have antiallergic properties and can be used, for example, for the treatment and prophylaxis of allergic diseases, such as asthma, hay fever, conjunctivitis, urticaria and eczema, is described in the examples.

The halogeno-benzofuranone-carboxylic acids obtained according to the invention can also be used for the preparation of biocidal active compounds. The active compounds are suitable for combating diverse plant and animal pests, in particular phytopathogenic bacteria and fungi, such as representatives of the classes Phycomycetes and Basiodiomycetes. In order to prepare such active compounds, the halogenocarboxymethylene-benzofuranones obtained according to the invention, in particular those in which $R_1$ and $R_2$ are hydrogen, $R_3$ is hydrogen or an alkyl group having 1–4 carbon atoms, especially the methyl group, and $R_4$ is hydrogen, a halogen atom or an alkyl group having 1–4 carbon atoms, are converted to 2-alkoxycarbonylhalogenomethylene-benzofuranones in a manner which is known per se. These 2-alkoxycarbonylhalogenomethylene-benzofuranones have, for example, both a preventive and a curative action against phytopathogenic fungi on crop plants, such as cereals, coffee, vegetables, sugarbeet, soya, groundnuts and ornamental plants, but in particular on vines and hops. The preparation of several biocidal active compounds is described in the examples.

EXAMPLE 1

250 ml of 1,2-dichloroethane and 265 g of powdered anhydrous $AlCl_3$ are initially introduced into a stirred flask provided with a HCl outlet. 54 g (0.5 mol) of m-kresol are then added at 20°–30° C. in the course of about 30 minutes, with stirring, and 87.5 g (0.5 mol) of 2,3-dichloromaleic anhydride (95% strength) are then added in the course of 1.5 hours. After stirring for a further 4 hours at room temperature (about 20°–25° C.), the reaction mixture is introduced into a mixture of 250 ml of concentrated hydrochloric acid, water and ice (end volume about 3 liters). The dichloroethane solution is separated off, 500 ml of water are added and the organic solvent is removed under reduced pressure in a rotary evaporator at a heating bath temperature of about 50° C. The residue is dissolved in 3 liters of water with the addition of 200 ml of sodium hydroxide solution (30% strength) and the solution is stirred for 10 minutes at 20°-25° C. and then clarified by filtration using a kieselguhr filter aid. The reaction product is precipitated from the filtrate at 0°-5° C. by adding excess hydrochloric acid and is filtered off and washed with a little water. After drying in vacuo at 60° C., this gives 95 g (79% of theory) of reddish-tinged yellow 2-carboxychloromethylene-6-methyl-[2H]-benzofuran-3-one; melting 162°-164° C.

According to the thin layer chromatogram, the product contains only slight impurities and can therefore be used direct for further reactions. When recrystallised from ethyl acetate, the product melts at 172°-174° C.

NMR spectrum (60 megahertz, δ values in ppm; solution in CDCl₃): 2.6 (s, 3H, —CH₃); 7.1 (m, 2H aromatic); 7.7 (d, 1 H aromatic J ~ 8 Hz); about 13.8 (broad signal, 1H, D₂O replaceable, —COOH).

The chemical analysis and the NMR spectrum correspond to the formula

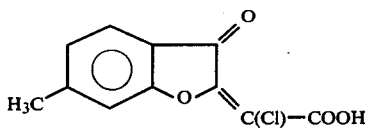

(2-carboxychloromethylene-6-methyl-[2H]-benzofuran-3-one).

The benzofuranes of the formula I listed in the table which follows were prepared in an analogous manner. In all of the examples, the cyclisation was carried out as described above.

Table

| Example No. | Compound of the formula II | X | Solvent | Reaction time hours | Reaction temperature ° C. | Compound of the formula I | Yield % of theory | Recrystallised from | Melting point °C. |
|---|---|---|---|---|---|---|---|---|---|
| 2 | 4-CH₃-phenol | X = Cl | CH₂Cl₂ | 4 | 20–30 | CH₃-benzofuran-C(Cl)COOH | 76 | ethylene glycol dimethyl ether | 197 |
| 3 | 2-CH₃-phenol | X = Cl | " | 4 | " | CH₃-benzofuran-C(Cl)COOH | 21 | ethyl acetate | 170–171 |
| 4 | phenol | X = Cl | " | 6 | " | benzofuran-C(Cl)COOH | 35 | 70% strength acetic acid | 168–169 |
| 5 | 4-CH₃-phenol | X = Br | 1,2-dichloroethane | 4 | " | CH₃-benzofuran-CH₃-C(Br)COOH | — | ethyl acetate | 190–191 |
| 6 | 3-CH₃-phenol | X = Br | " | 4 | " | CH₃-benzofuran-C(Br)COOH | — | — | 180–182 |
| 7 | 4-Et-phenol | X = Cl | " | 4 | " | H₅C₂-benzofuran-C(Cl)COOH | 80 | toluene | 146–147 |
| 8 | 2,4-di-CH₃-phenol | X = Cl | " | 1 | " | CH₃-benzofuran-CH₃-C(Cl)COOH | 69 | toluene | 208 |
| 9 | 3,5-di-CH₃-phenol | X = Cl | " | 1 | " | CH₃-benzofuran-CH₃-C(Cl)COOH | 63 | toluene | 214 |
| 10 | 4-cyclohexyl-phenol | X = Cl | " | 4 | " | cyclohexyl-benzofuran-C(Cl)COOH | 65 | cyclohexane | 119–122 |

Table-continued

| Example No. | Compound of the formula II | X | Solvent | Reaction time hours | Reaction temperature °C | Compound of the formula I | Yield % of theory | Recrystallised from | Melting point °C. |
|---|---|---|---|---|---|---|---|---|---|
| 11 | (indanol-OH) | X = Cl | CH₂Cl₂ | 4 | " | (product, Na salt sparingly soluble) | 44 | CH₃OH | 183 |
| 12 | (naphthol-OH) | X = Cl | " | 1 | " | (product) C(Cl)COOH*) | 90 | dioxane | 212–213 |
| 13 | (Cl-phenol-OH) | X = Cl | 1,2-dichloroethane | 18 | 75 | (product) | 76 | toluene | 159 |
| 14 | (Cl-phenol-OH) | X = Cl | " | 24 | 20–30 | (product) | 35 | toluene | 199 |
| 15 | (CH₃,Cl-phenol-OH) | X = Cl | " | 20 | " | (product) | 80 | CH₃OH | 185 |
| 16 | (CH₃,Cl,CH₃-phenol-OH) | X = Cl | " | 20 | " | (product) | 62 | CH₃OH | 206 |
| 17 | (pyrogallol) | X = Cl | " | 48 | " | (product) | 27 | H₂O | >250 |
| 18 | (trimethylphenol-OH) | X = Cl | " | 4 | " | (product) | 52 | ethyl acetate | 207 |
| 19 | (phloroglucinol) | X = Cl | " | 5 | 5 | (product) | 41 | C₂H₅OH/H₂O | >250 |

*)Cyclisation already takes place in acid solution

EXAMPLE 20

If, in Example 1, with an otherwise identical procedure, an equimolar amount of the acid chloride of monomethyl 2,3-dichloromaleate is used in place of 0.5 mol of 2,3-dichloromaleic anhydride, this gives 2-carboxychloromethylene-6-methyl[2H]benzofuran-3-one in a similar yield. The melting point of the crude product is 171° C.

EXAMPLE 21

120 g of powdered anhydrous AlCl₃ are reacted in 230 ml of 1,2-dichloroethane in the manner described in Example 1 with 33 g (0.3 mol) of resorcinol and 52.7 g (0.3 mol) of dichloromaleic anhydride (95% pure). After a reaction time of 3 hours at 45° C., the resulting viscous reaction mass which has expanded forming bubbles is stirred with 1.5 liters of water and 30 ml of concentrated hydrochloric acid and the mixture is filtered. The residue on the filter is then comminuted in a mixer to a fine aqueous suspension (volume about 1 liter) and this is stirred with the addition of 20 ml of concentrated hydrochloric acid for 16 hours. The reaction product is filtered off, washed with water and dried in vacuo at 60° C. Yield 52.5 g (72.5% of theory) of a slightly impure crude product. Recrystallisation from ethylene glycol monoethyl ether gives the compound of the formula

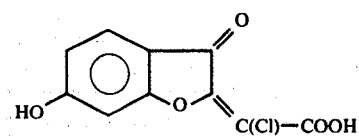

in the pure form; melting point 258° C. (2-carboxy-chloromethylene-6-hydroxy-[2H]-benzofuran-3-one).

NMR spectrum (60 megahertz, δ values in ppm; solution in (CD₃)₂SO): 6.7 (m, 2H aromatic, J∼2.5 Hz); 7.5 (d, 1H aromatic, J∼9 Hz); 12.5 (broad signal, 2H, replaceable D₂O, —OH and —COOH).

EXAMPLE 22

A mixture of 250 g of aluminium chloride, 45.5 g of sodium chloride, 15.3 g of potassium chloride and 48.3 g (0.29 mol) of dichloromaleic anhydride is melted together at 100° C. 37 g (0.25 mol) of m-N,N-dimethylaminophenol are then introduced slowly into the melt at 80° C. and the reaction mixture is stirred for 60 hours at 80° C. The viscous melt is now poured onto ice and the precipitate is filtered off. The latter is stirred in 900 ml of 1 N sodium hydroxide solution for 2 hours and the mixture is then acidified with concentrated hydrochloric acid. The crystals which have precipitated out are filtered off, rinsed with water and dried. After recrystallisation from acetic acid, 48.3 g (62.4% of theory) of 2-chlorocarboxymethylene-6-N,N-dimethylamino-[2H]-benzofuran-3-one of the formula

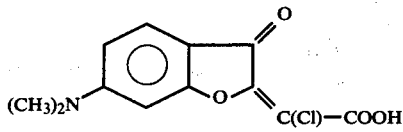

are obtained in the form of yellow crystals having a melting point of 225° C.

EXAMPLES 23–26

Using equimolar amounts of m-acetylaminophenol, 2,4-dimethyl-5-hydroxyphenol, 2,4-dichloro-3,5-dimethylphenol and 4-hydroxybenzoic acid, the following compounds are prepared in a manner analogous to that described in Example 22: 2-chlorocarboxymethylene-6-acetylamino-[2H]-benzofuran-3-one; melting point above 225° C. (reaction for 4 hours at 120° C.); 2-chlorocarboxymethylene-4-hydroxy-5,7-dimethyl-[2H]-benzofuran-3-one; melting point 225°–228° C. (reaction for 2 hours at 80° C., without treatment with dilute sodium hydroxide solution during working up, but recrystallised from acetic acid); 2-chlorocarboxymethylene-4,6-dimethyl-5,7-dichloro-[2H]-benzofuran-3-one having a melting point of 179°–180° C. (reaction for 1 hour at 80° C., without treatment with sodium hydroxide solution during working up, but recrystallised from 1,2-dimethoxyethane); and 2-chlorocarboxymethylene-5-carboxy-[2H]-benzofuran-3-one having a melting point of 132°–133° C. (reaction for 1.5 hours at 130° C., without after-treatment with dilute sodium hydroxide solution during working up; recrystallised from a 1:3 volume/volume mixture of 1,2-dimethoxyethane and water; the product crystallises with 0.5 mol of 1,2-dimethoxyethane).

I. Preparation of active compounds having pharmacological properties (antiallergic action)

(a) 16 g of 4-methyl-piperazine are added all at once to a suspension of 9.55 g of the 2-carboxychloromethylene-6-methyl-[2H]-benzofuran-3-one prepared according to Example 1 in 250 ml of isopropanol, at room temperature, with stirring, and the mixture is stirred for a further 16 hours at room temperature. After evaporating the volatile constituents under reduced pressure, the residual resin, which contains 2-carboxy-α-(4-methyl-piperazino)-methylene-6-methyl-[2H]-benzofuran-2-one of the formula

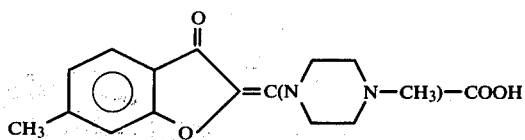

is dissolved in 150 ml of warm water, the solution is filtered with active charcoal and the filtrate is carefully rendered strongly acid with concentrated hydrochloric acid, with ice-cooling. An oily product precipitates and this soon crystallises on grinding. This gives 3-hydroxy-6-methylbenzofuryl-2-glyoxylic acid of the formula

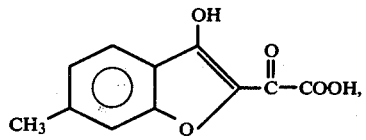

which after recrystallisation from a mixture of dimethyl formamide and water melts at 224°–226° C.

(b) A suspension of 120 g of 2-carboxychloromethylene-6-methyl[2H]benzofuran-3-one in 600 ml of water is neutralised to a pH of 7.0 by slowly adding an aqueous solution of sodium hydroxide and 150 ml of dimethyl sulphate are added dropwise at 20°–25° C. in the course of 5 hours, the pH value being kept between 6.7 and 7.0 by continually adding an approximately 10% strength aqueous solution of sodium carbonate, with stirring. The product is filtered off, washed with water and dried under reduced pressure at 60° C. This gives 2-methoxycarbonyl-chloromethylene-6-methyl[2H]benzofuran-3-one which according to chromatography is a single compound and which melts at 120°–121° C. after recrystallisation from ethanol.

33 g of a 33% strength ethanolic solution of dimethylamine are added all at once to a suspension of 20.2 g of 2-methoxycarbonylchloromethylene[2H]benzofuran-3-one in 800 ml of absolute ethanol, with stirring. The mixture is then stirred for a further 3 hours at 20°–25° C. After the reaction has ended, the reaction mixture is concentrated to a small volume under reduced pressure, after which 2-(α-dimethylamino-α-methoxycarbonyl-methylene)-6-methyl[2H]benzofuran-3-one crystallises out on grinding with a little water. After recrystallisation from a mixture of methylene chloride and petroleum ether, the products melts at 137°–139° C. A solution of 37.2 g of this product in 1,000 ml of 6 N hydrochloric acid is stirred at 20°–25° C. After 2 hours, the product which has precipitated out is filtered off and washed with water until neutral and the dried crude product is recrystallised from ethyl acetate. This gives methyl 3-hydroxy-6-methylbenzofuryl-2-glyoxylate; melting point 159°–161° C.

(c) 54 g of guanidine carbonate are added slowly to a suspension of 71.6 g of 2-carboxychloromethylene-5-methyl[2H]benzofuran-3-one in 500 ml of glacial acetic acid. The reaction mixture is kept at 60°–65° C. for 16 hours, with stirring, and then cooled to 20°–25° C., 200 ml of water are added and the product which has separated out is filtered off. This product is briefly heated to the boil in a mixture of 350 ml of ethanol and 350 ml of water and 200 ml of concentrated hydrochloric acid are added. The crystalline material is filtered off and washed with water. After drying under reduced pressure at 60° C., this gives 3-hydroxy-5-methylbenzofuryl-2-glyoxylic acid; melting point 239° C. (with decomposition).

(d) A mixture of 30 g of 3-hydroxy-5-methylbenzofuryl-2-glyoxylic acid, 250 ml of pure methanol and 0.6 ml of concentrated sulphuric acid is refluxed for 2 hours. The reaction mixture is added dropwise to ice-water (volume about 1,500 ml), the resulting mixture is neutralised to pH 7 with an aqueous solution of sodium carbonate, the precipitate is filtered off and the filter residue is dried at 60° C. under reduced pressure. This gives methyl 3-hydroxy-5-methylbenzofuryl-2-glyoxylate which, after recrystallisation from methanol, melts at 150°–151° C.

(e) Methyl 5,6-dimethyl-3-hydroxy-benzofuryl-2-glyoxylate (melting point 172°–173° C.) and methyl 3-hydroxy-5,6-trimethylene-benzofuryl-2-glyoxylate (melting point 189°–191° C.) can be prepared in an analogous manner starting from 2-carboxychloromethylene-5,6-dimethyl[2H]benzofuran-3-one and, respectively, 2-carboxychloromethylene-5,6-trimethylenebenzofuran-3-one.

The above active compounds (a)–(e) can be processed to tablets for oral use in a manner which is known per se.

(A) Tablets containing 0.1 g of active compound, for example methyl 3-hydroxy-6-methyl-benzofuryl-2-glyoxylate, are prepared as follows:

Composition (for 1,000 tablets)
active compound—100 g
lactose—50 g
wheat starch—73 g
colloidal silica—13 g
magnesium stearate—2 g
talc—12 g
water—q.s.

The active compound is mixed with a portion of the wheat starch and with the lactose and the colloidal silica and the mixture is forced through a sieve. A further portion of the wheat starch is mixed to a paste with five times the amount of water on a water bath and the above powder mixture is kneaded with this paste until a slightly plastic mass has formed. The plastic mass is pressed through a sieve of about 3 mm mesh width and dried and the dried granules are again forced through a sieve. The remaining wheat starch, the talc and the magnesium stearate are then mixed in and the resulting mixture is pressed to give tablets of 0.25 g.

(B) An approximately 2% strength aqueous solution, which is suitable for inhalation, of an active compound which is water-soluble in the free form or in the form of the sodium salt can be prepared, for example, in the following composition:

| Composition | |
|---|---|
| active compound, for example sodium (3-hydroxy-6-methylbenzofuryl-2)-glyoxylate | 2,000 mg |
| stabiliser, for example the disodium salt of ethylenediaminetetraacetic acid | 10 mg |
| preservative, for example benzalkonium chloride | 10 mg |
| water, freshly distilled to make up to | 100 ml |

Preparation

The active compound is dissolved in freshly distilled water with the addition of the equimolar amount of 2 N sodium hydroxide solution. The stabiliser and the preservative are then added. After all of the components have dissolved completely, the resulting solution is made up to 100 ml and filled into small bottles and these are sealed gas-tight.

II. Preparation of biocidal active compounds for combating phytopathogenic fungi and bacteria (f) 10 g of the 2-carboxy-chloromethylene-6-methyl-[2H]-benzofuran-3-one prepared according to Example 1, 100 ml of ethylene glycol monomethyl ether and 10 ml of concentrated sulphuric acid are heated at 60° C. for 7 hours. The reaction mixture is then added dropwise to ice-water and the pH of the resulting mixture is adjusted to about 8 by adding sodium carbonate. The resulting precipitate is filtered off, rinsed with water and dried. After recrystallisation from methanol, 2-[α-(2-methoxyethoxy)-carbonylchloromethylene]-6-methyl-[2H]-benzofuran-3-one of the formula

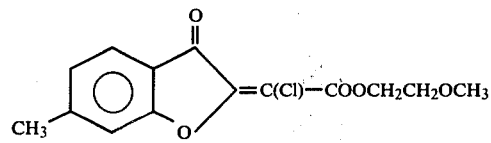

is obtained in a crystalline form; melting point 114°–115° C.

(g) A suspension of 48 g of the 2-carboxy-chloromethylene-5-methyl-[2H]-benzofuran-3-one prepared according to Example 2 in 260 ml of water is neutralised to pH 7 by adding sodium hydroxide solution. 60 ml of dimethyl sulphate are then added dropwise at 20°–25° C. in the course of 5 hours, with good stirring, the pH value being kept between 7 and 7.5 by adding sodium carbonate solution at the same time. The ester which has separated out (2-methoxycarbonyl-chloromethylene-5-methyl-[2H]-benzofuran-3-one) is filtered off, washed and dried in vacuo at 40° C. After recrystallisation from ethanol it melts at 79°–81° C.

The fungicidal action of the above active compounds (f) and (g) was tested as follows:

Action against *Puccinia triticina* on *Triticum vulgare*

6 days after sowing, wheat plants were sprayed with a spray mixture (0.05% by weight of active substance) prepared from a wettable powder of the active compound. After 24 hours the treated plants were infected with a uredo spore suspension of the fungus. After incubating for 48 hours at 95–100% relative atmospheric humidity and about 20° C., the infected plants were placed in a greenhouse at about 22° C. The development of rust pustules was assessed 12 days after infection.

Action against *Plasmopara viticola* on *Vitis vinifera*

Vine cuttings in a 6–8 leaf stage were sprayed with a spray mixture (0.05% by weight of active substance) prepared from a wettable powder of the active compound. After 24 hours the treated plants were infected with a sporangia suspension of the fungus. The infestation with fungus was assessed after incubating for 6 days at 95–100% relative atmospheric humidity and 20° C.

Active compounds (f) and (g) showed a good action.

What is claimed is:

1. A compound of the formula I

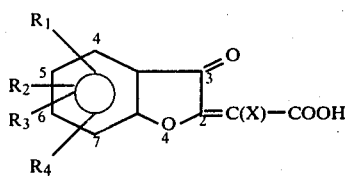

in which X is chlorine, bromine or fluorine, two of $R_1$ to $R_4$ independently of one another are hydrogen or lower alkyl, one of $R_1$ to $R_4$ is hydrogen, a halogen atom, hydroxyl or lower alkyl, and the last of $R_1$ to $R_4$ is hydrogen, a halogen atom, hydroxyl, carboxyl, lower alkyl, lower alkoxy, phenoxy, cycloalkyl of 5 to 8 carbon atoms, benzoyl; benzoyl substituted with alkyl of 1 to 4 carbon atoms, with alkoxy of 1 to 4 carbon atoms or with halogen; alkanoyl of 2 to 7 carbon atoms, amino, —$NQ_1Q_2$ or —$NHCOQ_3$; wherein $Q_1$ is hydrogen or lower alkyl, $Q_2$ is lower alkyl; or $Q_1$ and $Q_2$ together are alkylene of 4 to 7 carbon atoms, thiaalkylene of 4 to 7 carbon atoms, oxaalkylene of 4 to 7 carbon atoms or iminoalkylene of 4 to 7 carbon atoms where the imino group —$NQ_4$— has $Q_4$ as hydrogen or lower alkyl, and $Q_3$ is lower alkyl; or if two of $R_1$ to $R_4$ are hydrogen, the remaining two of $R_1$ to $R_4$ together are alkylene of 3 to 5 carbon atoms, which may be substituted by alkyl of 1 to 4 carbon atoms, which together with the bonding C atoms in the ortho-position form a cycloalkyl group having 5 to 7 ring members which may be substituted by alkyl of 1 to 4 carbon atoms; or together are 1,4-butadienyl which together with the bonding C atoms in the ortho position form a fused benzene ring.

2. A compound of the formula I according to claim 1, in which X is chlorine, $R_1$ and $R_2$ independently of one another are hydrogen or an alkyl group having 1-4 carbon atoms, $R_3$ is hydrogen, chlorine, fluorine, bromine or an alkyl group having 1-4 carbon atoms and $R_4$ is hydrogen, chlorine, fluorine, bromine, —OH, —COOH, cyclohexyl, an alkyl or alkoxy group having 1-4 carbon atoms, an alkanoyl group having 2-7 carbon atoms, an alkanoylamino group having 2-4 carbon atoms or a N,N-dialkylamino group having 1 or 2 carbon atoms in each alkyl part.

3. A compound of the formula I according to claim 1, in which X is chlorine, $R_3$ and $R_4$ are hydrogen and $R_1$ and $R_2$ together form an alkylene group having 3–5 carbon atoms which is bonded in the 5,6-position or a 1,4-butadienyl group bonded in the 4,5-position.

4. A compound according to claim 1 of the formula Ia

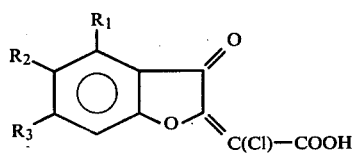

in which $R_1$ and $R_2$ independently of one another are hydrogen or alkyl having 1–4 carbon atoms and $R_3$ is hydrogen, alkyl or alkoxy having 1–4 carbon atoms or —OH, or in which $R_1$ and $R_2$ together form 1,4-butadienyl and $R_3$ is hydrogen or $R_1$ is hydrogen and $R_2$ and $R_3$ together form alkylene having 3 or 4 carbon atoms.

5. A compound of the formula Ia according to claim 4, in which $R_1$ is hydrogen or methyl and one of the radicals $R_2$ and $R_3$ is methyl and the other is hydrogen or methyl, or in which $R_1$ is hydrogen and $R_2$ and $R_3$ together are trimethylene.

6. A process for the preparation of a compound of the formula I according to claim 1, wherein a compound of the formula II

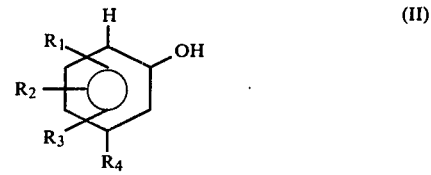

is reacted in the presence of a Lewis acid with a compound of the formula III

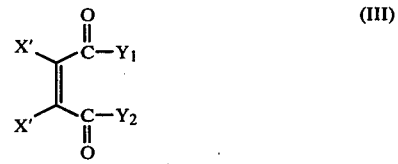

to give a compound of the formula IV

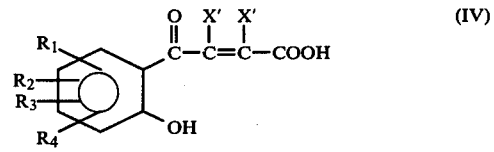

in which formulae $R_1$, $R_2$, $R_3$ and $R_4$ are as defined under formula I, the two X' in formula III and IV independently of one another are chlorine, fluorine or bromine and one of $Y_1$ and $Y_2$ is halogen and the other is —OH or —O—alkyl having 1-6 C atoms, or $Y_1$ and $Y_2$ together form the grouping —O—, and the compound of the formula IV is subsequently cyclised to a compound of the formula I.

7. A process according to claim 6, wherein dichloromaleic anhydride is used as the compound of the formula III.

8. A compound according to claim 1 of the formula

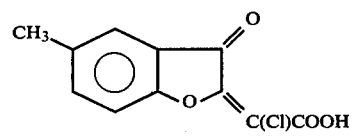

9. A compound according to claim 1 of the formula

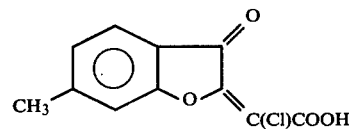

10. A compound according to claim 1 of the formula

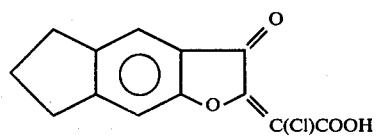

* * * * *